United States Patent
Mohr et al.

(10) Patent No.: US 6,649,754 B1
(45) Date of Patent: Nov. 18, 2003

(54) METHOD FOR PRODUCING MANNITOL

(75) Inventors: Thomas Mohr, Darmstadt (DE); Eugen Schwarz, Bensheim (DE); Peter-Johannes Mackert, Egelsbach (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/018,825

(22) PCT Filed: Jun. 14, 2000

(86) PCT No.: PCT/EP00/05454
§ 371 (c)(1),
(2), (4) Date: Dec. 21, 2001

(87) PCT Pub. No.: WO01/00550
PCT Pub. Date: Jan. 4, 2001

(30) Foreign Application Priority Data

Jun. 25, 1999 (DE) .......................................... 199 29 368

(51) Int. Cl.⁷ .................................................. C07H 1/00
(52) U.S. Cl. ...................................... 536/124; 536/1.11
(58) Field of Search ................................ 536/1.11, 124

(56) References Cited

U.S. PATENT DOCUMENTS 5,936,081 A   8/1999 Degelmann et al.

FOREIGN PATENT DOCUMENTS

| CA | 1114839 A | 12/1981 |
|---|---|---|
| EP | 0006313 A | 1/1980 |

OTHER PUBLICATIONS

Chemical Abstracts, vol. 118, No. 11, Mar. 15, 1993. Abstract No. 102391a.

Hegedus et al. "Stereoselective hydrogenation of D–fructos to D–mannitol on skeletal and supported copper–containing catalysts" Studies in Surface Science and Catalysis, Bd. 78, Heterogeneous Catalysis and Fine Chemicals III, 1993, pp. 187–194.

Makkee, et al.: "Hydrogenation of D–fructose and D–fructose/D–glucose mixtures" Carbohydrate Research, Bd. 138, Nr. 2, 15. Mai 1985 pp. 225–236.

Primary Examiner—James O. Wilson
Assistant Examiner—Ganapathy Krishnan
(74) Attorney, Agent, or Firm—Millen, White, Zelano & Branigan, P.C.

(57) ABSTRACT

A process for preparing mannitol from fructose is described and entails the hydrogenation of fructose taking place in the presence of a Raney copper catalyst and being carried out continuously.

15 Claims, No Drawings

METHOD FOR PRODUCING MANNITOL

The present invention relates to a process for preparing mannitol by hydrogenation of fructose. The hydrogenation takes place in the presence of a Raney copper catalyst and is carried out continuously.

Mannitol is used, for example, in tablet production and as sugar substitute.

Processes for preparing mannitol from fructose by hydrogenation on heterogeneous copper catalysts have already been disclosed.

Supported copper catalysts such as, for example, copper on silica gel show in the batchwise hydrogenation of 10% by weight aqueous fructose solution selectivities for mannitol of 60–65% [M. Makkee, A. P. G. Kieboom, H. Bekkum, Carbohydr. Res., 138 (1985) 225].

EP 0 006 313 makes use of supported copper catalysts for hydrogenation of the fructose in 20% by weight aqueous fructose solutions. The use of a copper/$SiO_2$ catalyst in the batchwise hydrogenation of fructose gives 60–65% yields of mannitol. Storage of such catalysts for some days must take place under a hydrogen atmosphere.

The batchwise hydrogenation of D-fructose to mannitol on powdered copper-containing structured catalysts and supported copper catalysts is described in the literature for the use of 20% aqueous fructose solutions at temperatures of 50–60° C. and a hydrogen pressure of 50–60 bar. The selectivities for mannitol are 60–65% for Raney copper catalysts with various modifications (for example doped with Co, Fe, B, Zn or Cr). Conversions of up to 97% are achieved with the Raney catalysts [M. Hegedus, S. Gobolos, J. L. Margitfalvi in "Heterogeneous Catalysis and Fine Chemicals III", M. Guisnet et al. (Ed.), 1993 Elsevier Publishers, 187–194; HU 60230].

DE 197 20 496 describes a process for hydrogenating sugars or sugar mixtures to sugar alcohols or sugar alcohol mixtures, where the sugars or sugar mixtures are hydrogenated in aqueous solution at elevated temperature and elevated pressure with hydrogen using a coated catalyst comprising a mixture of a pure Raney metal and a Raney metal alloy, and where the coated catalyst has a substantially catalytically inactive core which acts as support, and a catalytically active coating. In a batchwise process, 30% aqueous fructose solution is hydrogenated using a catalyst in tablet form consisting of a copper/aluminum alloy (Cu: Al equal to 50:50% by weight) and pure copper as binder in the ratio 100:15 by weight at 90° C. with a reaction time of 22 h, and a conversion of 98.4% is achieved. 61.6% by weight mannitol, 36.2% by weight sorbitol, 0.12% by weight glucose and 0.52% by weight other byproducts are formed.

It was an object of the present invention to develop a process for preparing mannitol from fructose, which avoids or at least reduces the disadvantages of known processes and, in particular, makes it possible to prepare mannitol from fructose with high conversions and with little byproduct formation in a short reaction time.

It has now been found, surprisingly, that this object is achieved when the process for preparing mannitol from fructose is carried out in such a way that the hydrogenation of fructose takes place in the presence of a Raney copper catalyst and is carried out continuously.

The invention thus relates to a process for preparing mannitol from fructose, characterized in that the hydrogenation of fructose takes place in the presence of a Raney copper catalyst and is carried out continuously.

The process according to the invention is distinguished in particular by the fact that the preparation of mannitol from fructose takes place with high conversions and with little byproduct formation in short reaction times.

The present invention provides an advantageous process for preparing mannitol by reduction or hydrogenation of fructose. In this process, an aqueous fructose solution is passed over a fixed bed of a Raney copper catalyst.

The fructose has a purity of 90–100%, preferably of 95–100%. The main impurity in this case is glucose. The Raney copper catalysts suitable for the process according to the invention can be purchased or can be prepared by known methods [see, for example, M. Hegedus, S. Göbölös, J. L. Margitfalvi in "Heterogeneous Catalysis and Fine Chemicals III", M. Guisnet et al. (Ed.), 1993 Elsevier Publishers, 187–194; HU 60230].

The Raney copper catalysts are prepared by grinding and screening a copper/aluminum alloy to the required particle size, and activating the surface by treatment with, for example, 10–20% aqueous sodium hydroxide solution at 20–80° C. This forms a coated catalyst which consists of an inactive core of Raney alloy and an active surface of the corresponding Raney metal. The thickness of the coating depends on the duration of the activation of the catalyst particles.

No binders for the Raney copper alloy, such as, for example, pure Raney metal, are used to prepare the catalysts used for the process according to the invention.

The catalysts used for the process according to the invention have the advantage that they can be prepared at very reasonable cost and straightforwardly. In addition, they do not have to be activated for the actual reaction by previous reduction and have high stability on storage under water.

The catalysts used for the process according to the invention may be doped, that is to say the copper/aluminum alloy may contain a total of 0.1–20% by weight of other elements such as, for example, boron, chromium, cobalt, iron, molybdenum, titanium or zinc.

The reaction can take place, for example, in a trickle-bed reactor. This entails a vertical tubular reactor being packed with the catalyst bed and the aqueous sugar solution trickling or flowing through co-currently with the hydrogen. In an alternative process, the aqueous sugar solution can flow through the catalyst bed, for example in a type of bubble column, from the bottom co-currently with the hydrogen.

In a preferred variant of the process, a temperature gradient is set up over a plurality of reactors connected in sequence, for example four reactors connected in sequence. In this variant of the process it is in turn advantageous for the hydrogenation in the first reactor to take place at relatively low initial temperatures and the hydrogenation of the remaining sugars in the following reactors to take place at higher temperatures. This makes it possible to keep the amount of byproducts below 1% by weight, with a conversion exceeding 99.8%.

Suitable reaction temperatures for the process according to the invention are temperatures between 50 and 180° C. The process according to the invention is preferably carried out at reaction temperatures of from 90 to 140° C.

Suitable hydrogen pressures for the process according to the invention are hydrogen pressures between 50 and 300 bar. The process according to the invention is advantageously carried out with hydrogen pressures of from 150 to 250 bar. The process according to the invention is particularly preferably carried out with hydrogen pressures of from 160 to 200 bar.

Suitable concentrations of fructose in water for the process according to the invention are concentrations of from 10 to 70% by weight. The process according to the invention is preferably carried out with concentrations of from 40 to 60% by weight fructose in water. The process according to the invention is particularly preferably carried out with concentrations of from 50 to 55% by weight fructose in water.

The high concentrations of the aqueous precursor solution which can be achieved on use of the process according to the invention have the advantage that only a small amount of water needs to be removed for working up the product solution. This makes it possible, for example, to reduce significantly the energy consumption compared with processes using lower precursor concentrations.

Suitable ratios of fructose to hydrogen for the process according to the invention are ratios of from 1 mol fructose:1 mol hydrogen to 1 mol fructose 100 mol hydrogen. The process according to the invention is preferably carried out with ratios of fructose to hydrogen of from 1 mol fructose:5 mol hydrogen to 1 mol fructose:40 mol hydrogen.

A suitable space velocity (ratio of volumetric flow of sugar solution to catalyst volume) for the process according to the invention is an LHSV of from $0.01\ h^{-1}$ to $10.0\ h^{-1}$. The process according to the invention is preferably carried out with an LHSV of from $0.01\ h^{-1}$ to $1.0\ h^{-1}$.

The process according to the invention is preferably carried out at a pH of from 3.0 to 12.0, in particular at a pH of from 4.0 to 6.0.

The progress and the end of the reaction, and the analysis of the reaction products, can take place, for example, by means of HPLC, for example using standard HPLC equipment with calcium ion exchanger columns.

After the reaction is complete, the reaction product is isolated by conventional methods. "Usual working up" means for the purpose of the present invention the following:

The reaction mixture is collected in a high-pressure separator and the hydrogen is recycled after replacement of the consumed hydrogen. The solution is then decompressed, normally having a temperature of about 90–95° C. It is filtered hot (at temperatures above 60° C.) to remove residues of catalyst and is then purified on anion and cation exchanger resins to remove ionic impurities.

Isolation of mannitol from the purified hydrogenation solution can then take place by crystallizing the mannitol from the mother liquor or by chromatographic separation of the two main products mannitol and sorbitol.

Even without further statements, it is assumed that a skilled person is able to make use of the above description to the widest extent. The preferred embodiments are therefore to be regarded merely as descriptive, and by no means as in any way limiting, disclosure.

The complete disclosure in all the applications and publications mentioned hereinbefore and hereinafter is incorporated into this application by reference.

The following examples are intended to illustrate the present invention. However, they are by no means to be regarded as limiting.

EXAMPLES

A commercially available Raney copper fixed bed catalyst (Al: 39.0%; Cu: 61.0%) is used. The particle size of the irregularly shaped particles is about 2×3 mm. The catalyst bed has a free volume of about 50%, and the apparent density is about $1.75\ g/cm^3$.

The reaction is monitored and the reaction products are analysed by HPLC.

Example 1

A fructose solution is hydrogenated in a continuous fixed bed process in a hydrogenation reactor with a volume of 120 ml. The tubular reactor consists of a vertical stainless steel tube with a length of 25 cm and an internal diameter of 2.5 cm. A perforated metal plate is located at the bottom of the reactor, and hydrogenation solution and hydrogen are fed in co-currently from the top (trickle bed reactor).

The tubular reactor contains 241.5 g of (moist) Raney copper catalyst. With a volume of 120 ml for the tubular reactor, the flow rate of fructose solution (50% by weight aqueous solution) is 60 ml/h (LHSV=$0.5\ h^{-1}$). The pressure is 170 bar and the temperature is 110° C. A hydrogen flow rate of 75 l (STP)/h is applied. The purity of the fructose used is 100%. The results of the HPLC analysis are shown in Table 1.

Example 2

The reaction is carried out as described in Example 1. However, a precursor which consists of 96.0% by weight of fructose is used in place of a pure fructose solution. The results of the HPLC analysis are a shown in Table 1.

TABLE 1

| | Example 1 | | Example 2 | |
|---|---|---|---|---|
| Component | Precursor [% by weight] | Product [% by weight] | Precursor [% by weight] | Product [% by weight] |
| Fructose | 100.0 | 1.4 | 96.0 | 5.4 |
| Glucose | — | 0.1 | 3.7 | 0.8 |
| Sucrose | — | — | 0.3 | 0.1 |
| Mannitol | — | 62.8 | — | 57.9 |
| Sorbitol | — | 35.4 | — | 35.5 |
| Other byproducts | — | 0.3 | — | 0.3 |

The ratio of mannitol to sorbitol is reduced in Example 2 because the glucose content of the precursor is hydrogenated to sorbitol.

What is claimed is:

1. A continuous process for preparing mannitol from fructose wherein the concentration of fructose in water is 50%–55%, by weight, comprising hydrogenating fructose in the presence of a Raney copper and aluminum catalyst without a binder comprising a copper-aluminum ratio of 61:39 wt. % prepared by grinding a copper/aluminum alloy to an effective particle size and activating the surface with a 10–20% aqueous sodium hydroxide solution at 20–80° C. wherein the space velocity is an LSHV of $0.5\ h^{-1}$–$10.0\ h^{-1}$.

2. A process according to claim 1, wherein the process is carried out in aqueous medium.

3. A process according to claim 1, wherein the process is carried out at a reaction temperature of 50° C.–180° C.

4. A process according to claim 1, wherein the process is carried out at a hydrogen pressure of 50 bar–300 bar.

5. A process according to claim 1, wherein the concentration of fructose in water is 10%–70%, by weight.

6. A process according to claim 1, wherein the catalyst is doped with 0.1–20%, by weight, of an element of boron, chromium, cobalt, iron, molybdenum, titanium, or zinc.

7. A process according to claim 1, wherein a reaction takes place in a trickle-bed reactor.

8. A process according to claim 1, wherein a reaction takes place in a bubble column.

9. A process according to claim 1, wherein the process is carried out at a reaction temperature of 90° C.–140° C.

10. A process according to claim 1, wherein the process is carried out at a hydrogen pressure of 150 bar–250 bar.

11. A process according to claim 1, wherein the process is carried out at a hydrogen pressure of 160 bar–200 bar.

12. A process to claim 1, wherein the mol ratio of fructose:hydrogenis 1:1–1:100.

13. A process according to claim 1, wherein the space velocity is an LSHV of 0.1 h$^{-1}$–1.0$^{-1}$.

14. A process according to claim 1, wherein the process is at a pH of 3.0–12.0.

15. A process according to claim 1, wherein the process is at a pH of 4.0–6.0.

* * * * *

UNITED STATES PATENT AND TRADEMARK OFFICE
CERTIFICATE OF CORRECTION

PATENT NO.    : 6,649,754 B1
DATED         : November 18, 2003
INVENTOR(S)   : Thomas Mohr et al.

It is certified that error appears in the above-identified patent and that said Letters Patent is hereby corrected as shown below:

Column 5,
Line 2, reads "hydrogenis" should read -- hydrogen is --

Signed and Sealed this

Seventh Day of September, 2004

JON W. DUDAS
*Director of the United States Patent and Trademark Office*